US009855351B2

(12) United States Patent
Kim (10) Patent No.: US 9,855,351 B2
(45) Date of Patent: Jan. 2, 2018

(54) STERILIZATION APPARATUS FOR PORTABLE ELECTRONIC DEVICE (71) Applicant: Seoul Viosys Co., Ltd., Ansan-si (KR)

(72) Inventor: Jong Rack Kim, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 14/838,150

(22) Filed: Aug. 27, 2015

(65) Prior Publication Data
US 2016/0074545 A1 Mar. 17, 2016

(30) Foreign Application Priority Data

Sep. 11, 2014 (KR) .................. 10-2014-0120041

(51) Int. Cl.
A61L 2/10 (2006.01)
H04R 1/12 (2006.01)
H04R 1/02 (2006.01)

(52) U.S. Cl.
CPC ............... *A61L 2/10* (2013.01); *H04R 1/028* (2013.01); *H04R 1/12* (2013.01)

(58) Field of Classification Search
CPC .......... A61L 2/10; A61L 2/24; A61L 2202/14; A61L 9/20; A61L 2202/122; A61L 2/0047
See application file for complete search history.

(56) References Cited

U.S. PATENT DOCUMENTS

| 2,822,476 | A | * | 2/1958 | Osgood | ..................... | A61L 2/10 |
| | | | | | | 250/455.11 |
| 5,126,572 | A | * | 6/1992 | Chu | ...................... | A46B 17/04 |
| | | | | | | 250/455.11 |
| 8,203,124 | B2 | * | 6/2012 | Havens | ..................... | A61L 2/10 |
| | | | | | | 250/455.11 |
| 8,481,970 | B2 | * | 7/2013 | Cooper | ..................... | A61L 2/10 |
| | | | | | | 250/453.11 |
| 9,205,159 | B2 | * | 12/2015 | Kim | .......................... | A61L 2/10 |
| 2006/0008400 | A1 | * | 1/2006 | Gutman | .................... | A23L 3/28 |
| | | | | | | 422/292 |
| 2007/0023710 | A1 | * | 2/2007 | Tom | ......................... | A61L 2/10 |
| | | | | | | 250/504 R |

(Continued)

FOREIGN PATENT DOCUMENTS

| KR | 1020150050334 | 5/2015 |
| KR | 1020150056449 | 5/2015 |

(Continued)

OTHER PUBLICATIONS

Weigl, C., Examiner, DPMA, Office Action, German Patent Application No. 102015115038.7, Jul. 7, 2016, 12 pages.

(Continued)

*Primary Examiner* — Wyatt Stoffa
(74) *Attorney, Agent, or Firm* — Perkins Coie LLP (57) ABSTRACT A sterilization apparatus for a portable electronic device may include: a case having an opening receiving a portable electronic device; an ultraviolet (UV) irradiation unit arranged in the case, and configured to sterilize the portable electronic device by irradiating UV light onto the portable electronic device; a door connected to the case for opening and closing the opening of the case; and a display unit connected to the portable electronic device, and configured to display an image outputted from the portable electronic device.

22 Claims, 8 Drawing Sheets (56) References Cited

U.S. PATENT DOCUMENTS

| | | | | |
|---|---|---|---|---|
| 2008/0067418 | A1* | 3/2008 | Ross | A61L 2/10 250/455.11 |
| 2009/0257912 | A1* | 10/2009 | Lane | A61L 2/24 422/24 |
| 2012/0194738 | A1* | 8/2012 | Wang | G06F 1/1632 348/552 |
| 2012/0328474 | A1* | 12/2012 | Campagna | A61L 2/10 422/23 |
| 2013/0004367 | A1* | 1/2013 | Roberts | A61L 2/10 422/24 |
| 2013/0063922 | A1* | 3/2013 | La Porte | A61L 2/10 361/807 |
| 2014/0097353 | A1* | 4/2014 | Ben-Hur | A61M 1/3681 250/430 |
| 2014/0183377 | A1* | 7/2014 | Bettles | A61L 2/10 250/455.11 |
| 2015/0137762 | A1* | 5/2015 | Kim | H02J 7/0044 320/115 |

FOREIGN PATENT DOCUMENTS

| | | |
|---|---|---|
| KR | 1020150057299 | 5/2015 |
| TW | M383144 U1 | 6/2010 |
| WO | 2012100660 | 8/2012 |
| WO | 2013040260 | 3/2013 |

OTHER PUBLICATIONS

Office Action in Taiwan Application No. 10412588 dated Feb. 6, 2017 (with English summary), 5 pages.

\* cited by examiner

STERILIZATION APPARATUS FOR PORTABLE ELECTRONIC DEVICE

CROSS-REFERENCES TO RELATED APPLICATIONS

This patent document claims priority to Korean application number 10-2014-0120041, filed on Sep. 11, 2014, which is incorporated by reference in its entirety.

TECHNICAL FIELD

The present disclosure relates to a sterilization apparatus for a portable electronic device. For example, some implementation of the present disclosure relate to a sterilization apparatus for a portable electronic device, which is capable of easily sterilizing a portable electronic device.

BACKGROUND

In general, a portable electronic device can store and transmit data while performing wireless and wired communication. The portable electronic device may include various types of devices such as smart phone, E-book, digital camera, and tablet PC. Since the portable electronic device is carried and used by a user, the portable electronic device may be contaminated by sweat and body fluid of the user and surrounding contaminants. When the portable electronic device is contaminated, the portable electronic device may be harmful for the health of the user. Furthermore, when the user is exposed to the contaminated portable electronic device, the user may be infected by various viruses or germs.

SUMMARY OF THE INVENTION

Embodiments of the disclosed technology are directed to a sterilization apparatus for a portable electronic device, which is capable of easily sterilizing a portable electronic device.

In one embodiment, a sterilization apparatus for a portable electronic device is provided to include: a case having an opening receiving a portable electronic device; an ultraviolet (UV) irradiation unit arranged in the case, and configured to sterilize the portable electronic device by irradiating UV light onto the portable electronic device; a door connected to the case for opening and closing the opening of the case; and a display unit connected to the portable electronic device, and configured to display an image outputted from the portable electronic device.

In some implementations, the sterilization apparatus of claim 1, further comprising: a first connector installed in the case and connected to a connector of the portable electronic device; and a second connector installed in the door and connected to the first connector and the display unit.

In some implementations, when the door is closed, the first and second connectors are connected to each other.

In some implementations, the sterilization apparatus further comprises a third connector installed in the case to connect the portable electronic device to an external electronic device.

In some implementations, the display unit comprises: a beam projector installed on the door, connected to the second connector, and configured to project an image outputted from the portable electronic device; and a screen installed in the case and displaying the image projected from the beam projector.

In some implementations, the case includes a housing groove formed at one side of the case and housing the screen, and the screen is installed to be movable upward or downward along the housing groove.

In some implementations, the UV irradiation unit is installed on the bottom of the case.

In some implementations, the sterilization apparatus further comprises additional UV irradiation unit arranged on the door to provide UV radiation to the portable electronic device.

In some implementations, the UV irradiation unit comprises: a printed circuit board; and UV LEDs mounted on the printed circuit board to irradiate UV light onto the portable electronic device.

In some implementations, the housing groove has a stepped part formed at the top of the housing groove with greater width that the housing groove, and the stepped part is configured to support the bottom of the screen such that the screen is prevented from descending from the housing groove.

In another aspect, a sterilization apparatus for a portable electronic device is provided to include: a case having a bottom portion with sidewalls extending up from the bottom portion and configured to provide a space inside the case for mounting a portable electronic device, wherein the case provides a first connector connected with the portable electronic device; a UV LED arranged in the case and configured to provide UV radiation to the portable electronic device; and a cover arranged around a top portion of the case and providing a second connector connected with the first connector, wherein the connection between the first and second connectors allows the UV LED irradiating UV light, wherein the sterilization apparatus further includes a screen inserted into a groove formed at one sidewall of the case and displaying information of the portable electronic device during the sterilization.

In some implementations, the sterilization apparatus further comprises a third connector provided in the case and connected to an external electronic device.

In some implementations, the screen is movable along the sidewall of the case.

In some implementations, information of the portable electronic device includes receiving a phone call or exchanging data with another device.

In some implementations, the sterilization apparatus further comprises a beam projector provided in the cover and connected to the portable electronic device and the screen, the beam projector projecting a screen of the portable electronic device onto the screen of the sterilization apparatus.

In some implementations, the case provides a stepped part formed at a top portion of the groove with a greater width than the groove.

In some implementations, the cover is configured to selectively cover the top portion.

In some implementations, the sterilization apparatus further comprises an additional UV LED arranged in the cover to provide UV radiation to the portable electronic device.

In some implementations, the sterilization apparatus further comprises a speaker provided in the case or the cover.

In some implementations, the screen has protrusions protruding to outside and formed at both sides of the screen.

DESCRIPTION OF SPECIFIC EMBODIMENTS

Embodiments of the disclosed technology will hereinafter be described in detail with reference to the accompanying drawings. It should be noted that the drawings are not to precise scale and may be exaggerated in thickness of lines or sizes of components for descriptive convenience and clarity only. Furthermore, the terms as used herein are defined by taking functions of the disclosed technology into account and can be changed according to the custom or intention of users or operators. Therefore, definition of the terms should be made according to the overall disclosures set forth herein.

In the present specification, when an element is referred to as being 'over' or 'under' another element, it may indicate that the former element is directly positioned 'over' or 'under' the latter element or an additional element is interposed therebetween. In the present specification, the terms such as 'upper' and 'lower' are the relative concept set from the viewpoint of an observer. Thus, when the viewpoint of the observer is changed, 'upper' may indicate 'lower, and 'lower' may indicate 'upper'.

In the plurality of drawings, like reference numerals represent substantially the same elements. Furthermore, the terms of a singular form may include plural forms unless referred to the contrary, and the term such as 'include' or 'have' specifies the existence of a property, a number, a step, an operation, a component, a part, or a combination thereof, and does not exclude one or more other properties, numbers, steps, operations, components, or combinations thereof.

The following embodiments of the present disclosure provide a sterilization apparatus for a portable electronic device, which is capable of easily sterilizing a portable electronic device.

Figure 1:
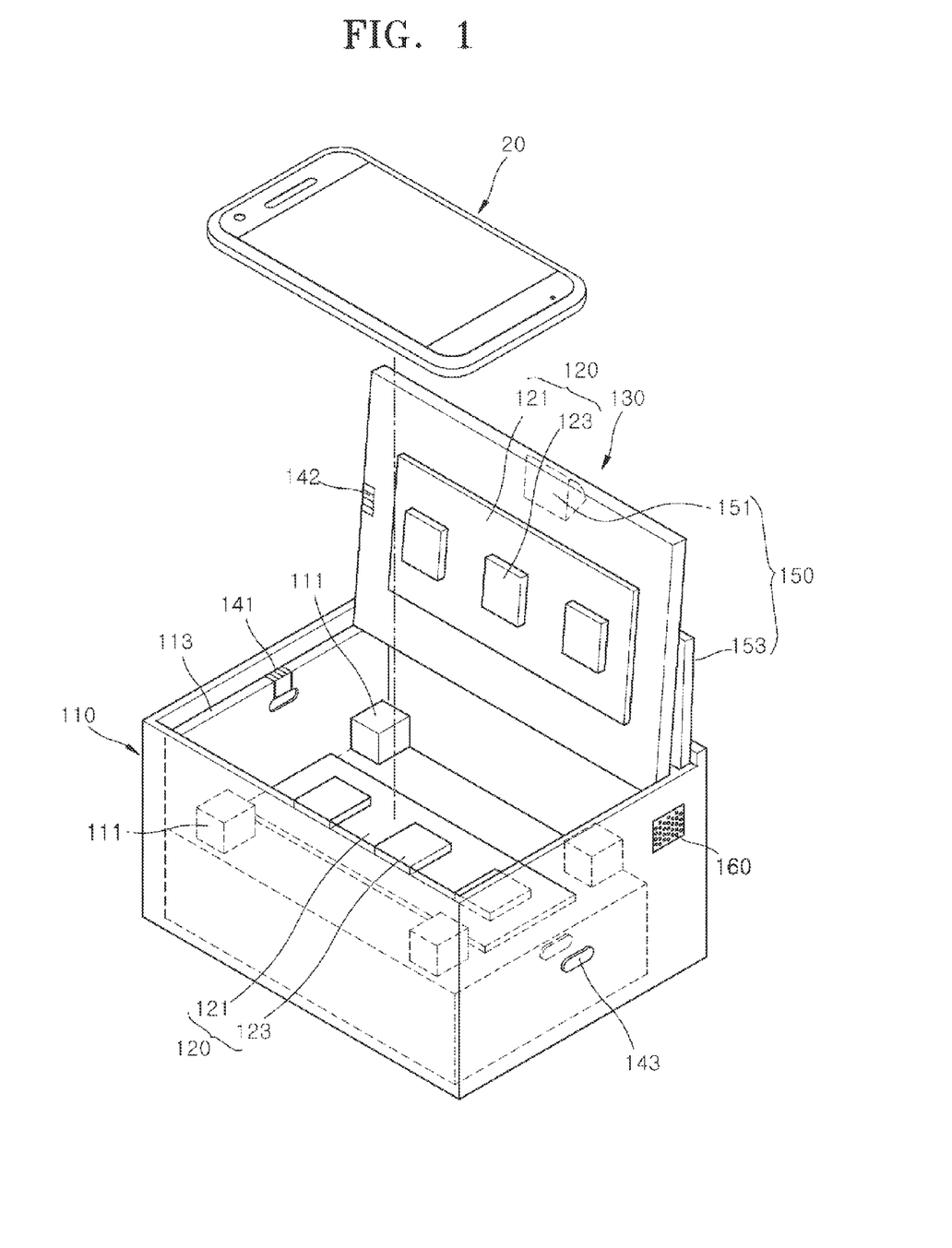
FIG. 1 is a schematic perspective view of an exemplary sterilization apparatus for a portable electronic device in accordance with an embodiment of the present disclosure.
Figure 2:
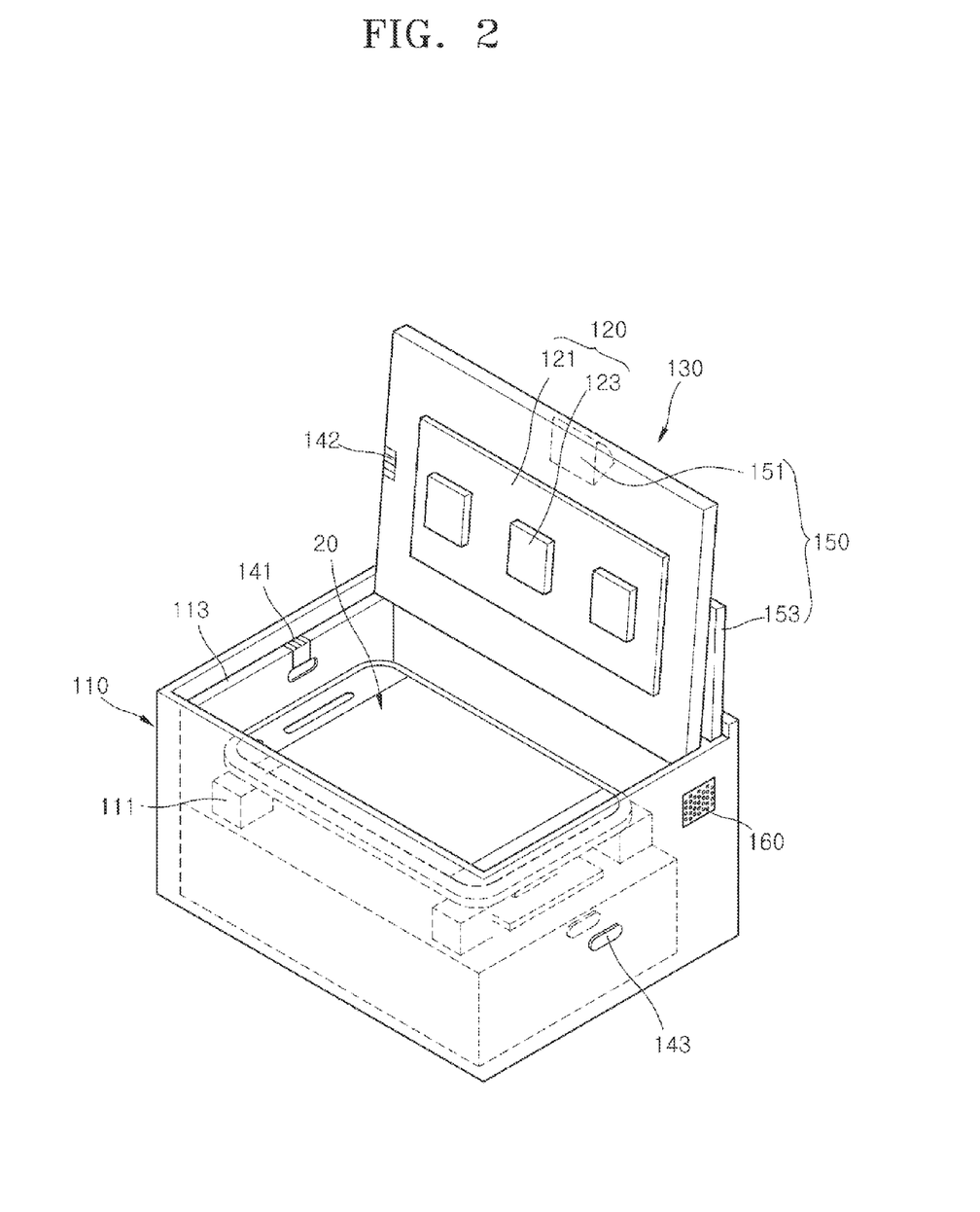
FIG. 2 is a schematic perspective view illustrating a state in which a portable electronic device is put into a case of the sterilization apparatus for a portable electronic device in accordance with the embodiment of the present disclosure.
Figure 3:
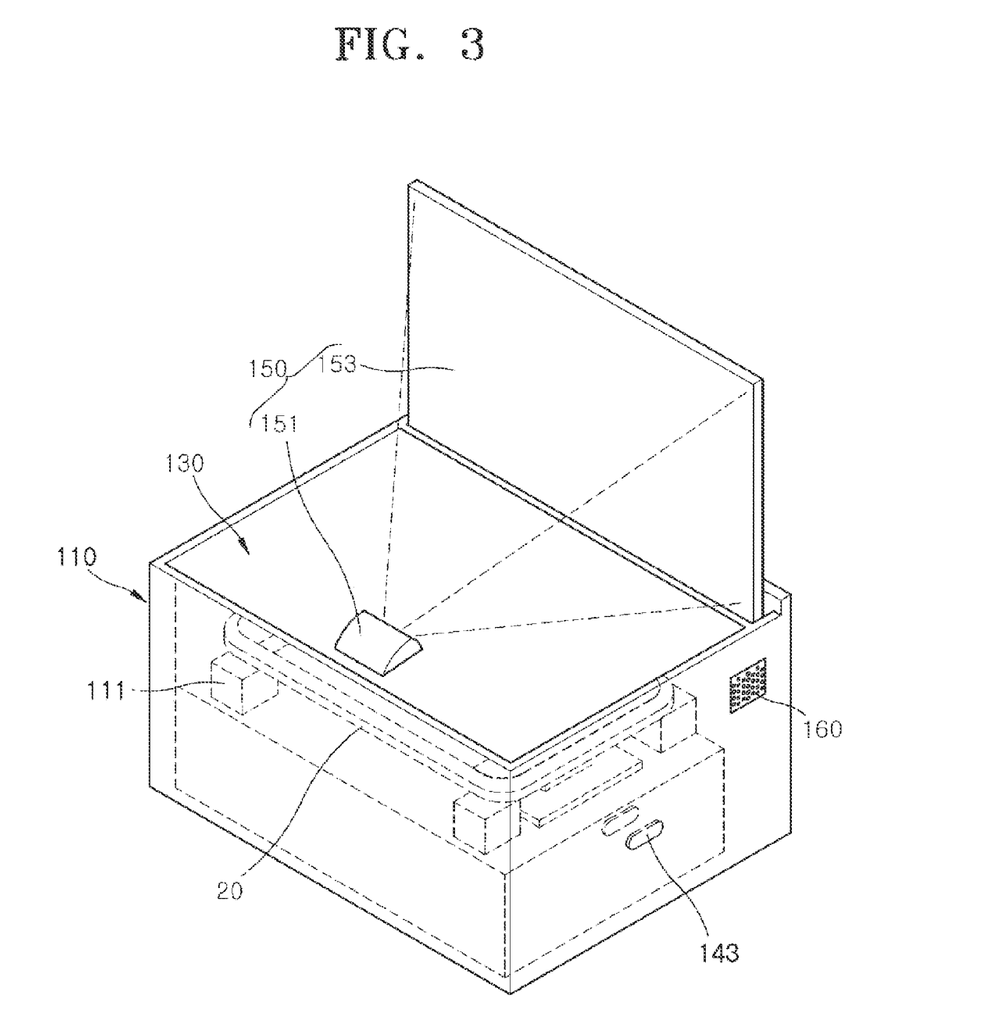
FIG. 3 is a schematic perspective view illustrating a state in which a display unit is operated after a portable electronic device is put into the case of a sterilization apparatus for a portable electronic device in accordance with the embodiment of the present disclosure.
Figure 4:
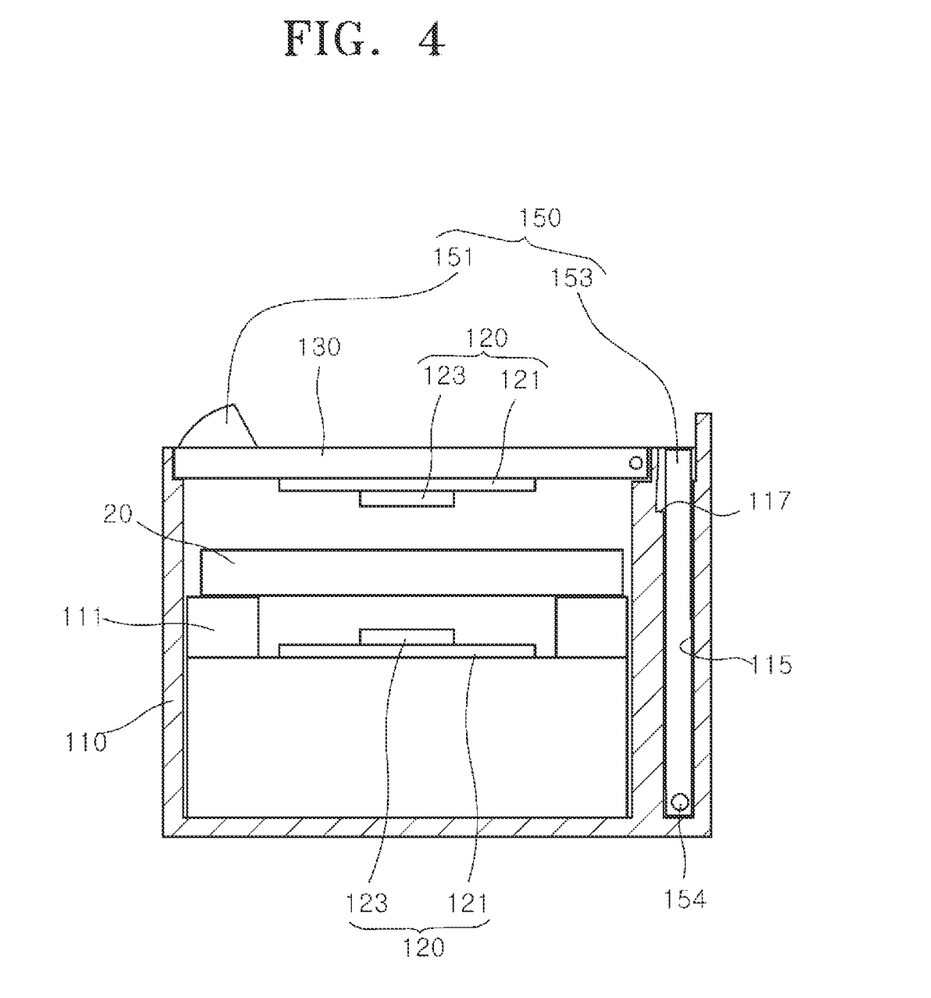
FIG. 4 is a schematic cross-sectional view of an exemplary sterilization apparatus for a portable electronic device in accordance with the embodiment of the present disclosure.

FIG. 1 is a schematic perspective view of a sterilization apparatus for a portable electronic device in accordance with an embodiment of the present disclosure. FIG. 2 is a schematic perspective view illustrating a state in which a portable electronic device is put into a case of the sterilization apparatus for a portable electronic device in accordance with the embodiment of the present disclosure. FIG. 3 is a schematic perspective view illustrating a state in which a display unit of the sterilization apparatus is operated after the portable electronic device is put into the case of the sterilization apparatus for a portable electronic device in accordance with the embodiment of the present disclosure. FIG. 4 is a schematic cross-sectional view of the sterilization apparatus for a portable electronic device in accordance with the embodiment of the present disclosure.

Referring to FIGS. 1 to 4, the sterilization apparatus for a portable electronic device may include a case 110, an ultraviolet (UV) irradiation unit 120, a door 130, and a display unit 150.

The case 110 may have an opening providing a space inside the case for receiving the portable electronic device 20. The case 110 may be formed in a rectangular box shape. The case 110 may include support parts 111 formed at the bottom of the case so as to support the bottom of the portable electronic device 20. The support parts 111 may be formed in various shapes, as long as the support parts 111 can support the portable electronic device 20. The case 110 may have a locking jaw 113 formed on the inner surface thereof so as to support the edge of the door 130. When the door 130 is closed, the door 130 may be stably supported by the locking jaw 113 of the case 110. Furthermore, the case 110 may include an operation button (not illustrated) for driving and stopping the sterilization apparatus for a portable electronic device.

The UV irradiation unit 120 may be arranged in the case 110, and sterilize the portable electronic device 20 by irradiating UV light onto the portable electronic device 20. Since the UV irradiation unit 120 sterilizes the portable electronic device 20, the portable electronic device 20 can be hygienically used.

The UV irradiation unit 120 may be installed on the door 130 and the bottom of the case 110 so as to face both sides of the portable electronic device 20. Since the UV irradiation unit 120 is installed on the door 130 and the bottom of the case 110, both sides of the portable electronic device 20 can be sterilized at the same time.

The UV irradiation unit 120 may include a printed circuit board 121 and UV LEDs 123 which are mounted on the printed circuit board 121 and irradiate UV light onto the portable electronic device 20. Since the UV LEDs 123 emit UV light, UV light having a waveform which is the most efficient for sterilization may be intensively emitted. Thus, the sterilization performance for the portable electronic device 20 can be improved. The LEDs 123 may be arranged in a line or a plurality of lines on the printed circuit board 121. The UV irradiation unit 120 may receive electricity from an external power supply or battery.

The door 130 may be installed to open or close the opening of the case 110. At this time, the door 130 may be installed at the top of the case 110 so as to be rotated through a hinge part. When the UV irradiation unit 120 irradiates UV light onto the portable electronic device 20, the door 130 may close the opening of the case 110, thereby preventing a user from being exposed to the UV light.

The case 110 or the door 130 may include a speaker 160 installed therein. The speaker 160 and the portable electronic device 20 may be connected to each other through a speaker connector (not illustrated). Thus, while the portable electronic device 20 is sterilized, the speaker 160 may be driven by the portable electronic device 20 such that the user can listen to music or voice.

Referring back to FIGS. 1 to 4, a first connector 141 may be installed in the case 110. The first connector 141 may be connected to a connector (not illustrated) of the portable electronic device 20. For example, connection parts (not illustrated) may be connected to both ends of a connection cable (not illustrated). One connection part may be connected to the connector of the portable electronic device 20, and the other connection part may be connected to the first connector 141.

The door 130 may include a second connector 142 installed therein. The second connector 142 may be connected to the first connector 141. For example, when the door 130 is closed, the second connector 142 may be connected to the first connector 141. Since the first and second connectors 141 and 142 are connected to each other when the door 130 is closed, a separate connection cable does not need to be installed in order to connect the first and second connectors 141 and 142 to each other. Thus, the number of parts of the sterilization apparatus for a portable electronic device can be reduced. Furthermore, when the first and second connectors 141 and 142 are connected to each other after the door 130 is closed, power may be applied to the UV LEDs 123. Thus, when the door 130 is closed, the UV LED 123s may irradiate UV light to automatically sterilize the portable electronic device 20. When the first and second connectors 141 and 142 are connected to each other, a beam projector 151 may be driven to display the screen of the portable electronic device on a screen 153.

The case 110 may include a third connector 143 installed in the case. The third connector 143 may be connected to the connector (not illustrated) of the portable electronic device 20, and connected to an external electronic device. Thus, while the portable electronic device 20 is sterilized, the external electronic device and the portable electronic device 20 may exchange data with each other. Furthermore, while the portable electronic device 20 is sterilized, a user may input data to the portable electronic device 20 using an input device such as a keyboard. Furthermore, a charging connector (not illustrated) of a charger (not illustrated) may be connected to the third connector 143 such that the portable electronic device 20 can be charged. Furthermore, the portable electronic device 20 may be wirelessly charged.

The display unit 150 may be installed in the door 130 and the case 110. The display unit 150 may be connected to the portable electronic device 20 through the second connector 142. The display unit 150 may display an image outputted from the portable electronic device 20. For example, when a phone call is received while the portable electronic device 20 is sterilized, the screen of the portable electronic device 20 may be displayed through the display unit 150. Furthermore, when the portable electronic device 20 and the external electronic device 50 exchange data with each other while the portable electronic device 20 is sterilized, the screen of the portable electronic device 20 may be displayed on the display unit 150. Thus, while the portable electronic device 20 is sterilized in the case 110, the user can watch the screen of the portable electronic device 20 through the display unit 150.

The display unit 150 may include the beam projector 151 and the screen 153. The beam projector 151 may be installed on the door 130. The beam projector 151 may be connected to the second connector 142, and project an image outputted from the portable electronic device 20. The screen 153 may be installed on the case 110. The image projected by the beam projector 151 may be displayed on the screen 153. Since the beam projector 151 projects an image outputted from the portable electronic device 20 onto the screen 153, the user can check the screen 153 of the portable electronic device 20 while the portable electronic device 20 is sterilized.

Figure 5:
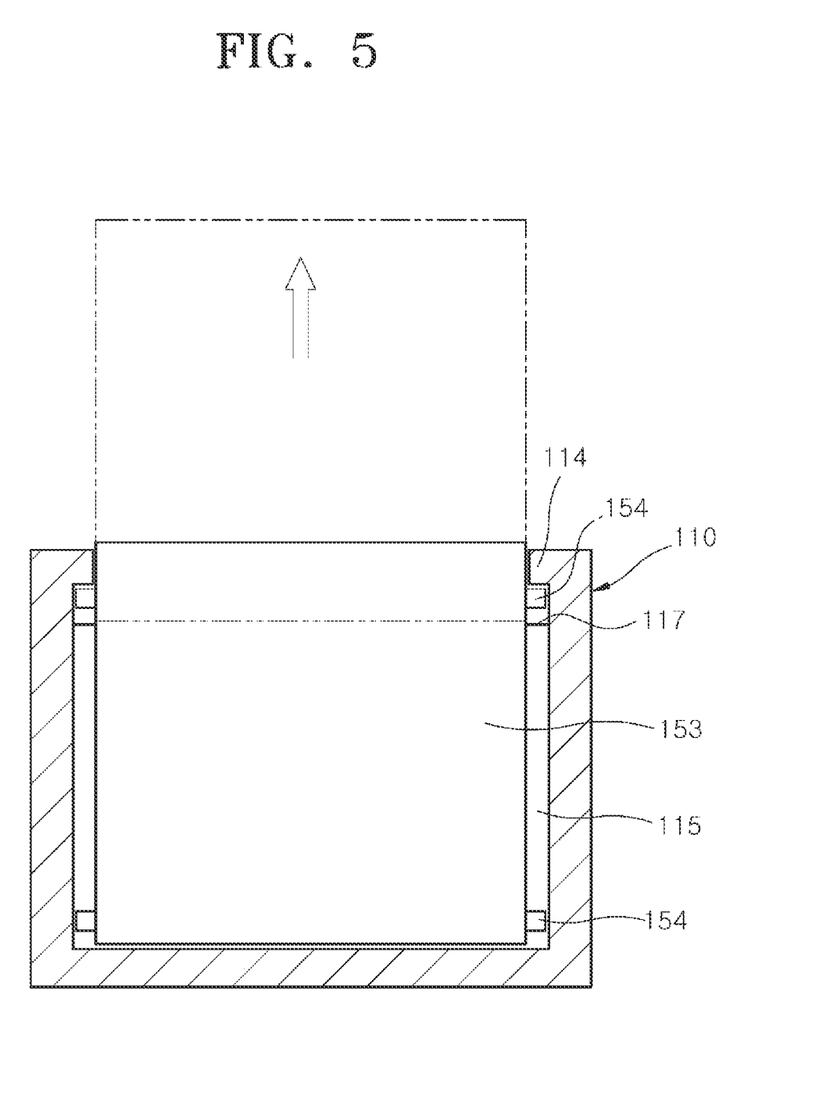
FIG. 5 is a schematic cross-sectional view illustrating a coupling structure of a screen of a sterilization apparatus for a portable electronic device in accordance with the embodiment of the present disclosure.
Figure 6:
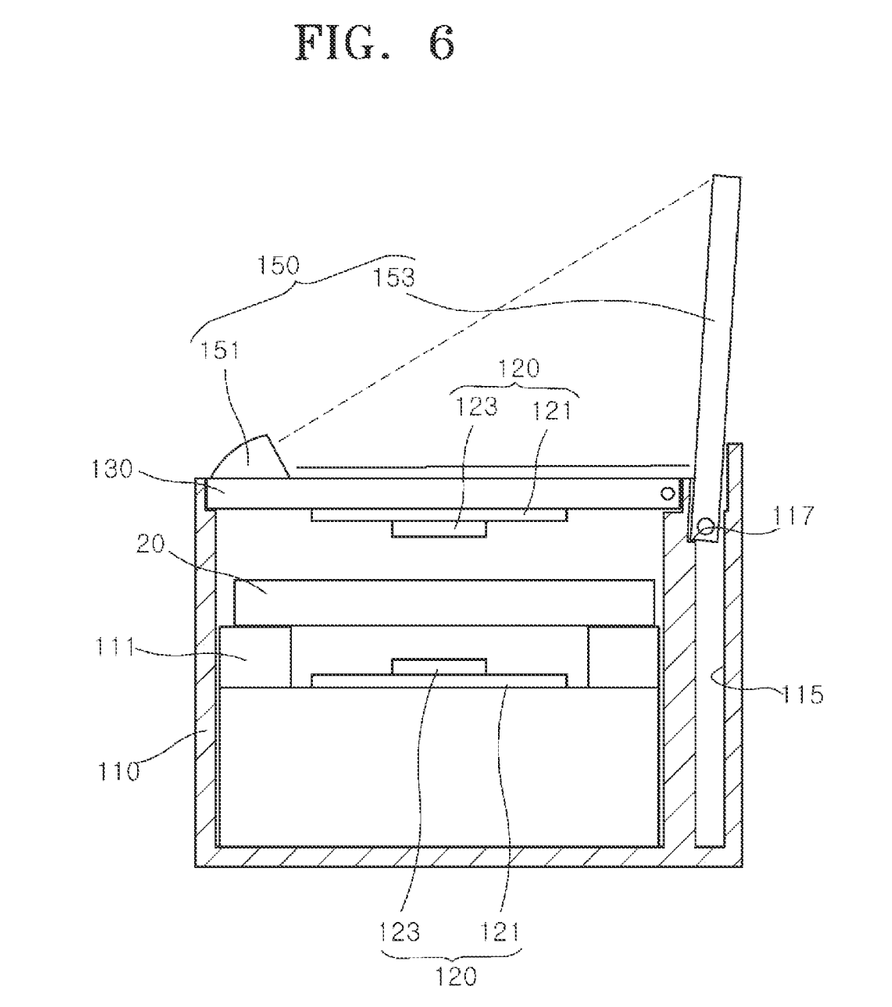
FIG. 6 is a schematic side view illustrating a state in which a display unit of a sterilization apparatus is operated after a portable electronic device is put into the case of the sterilization apparatus for a portable electronic device in accordance with the embodiment of the present disclosure.
Figure 7:
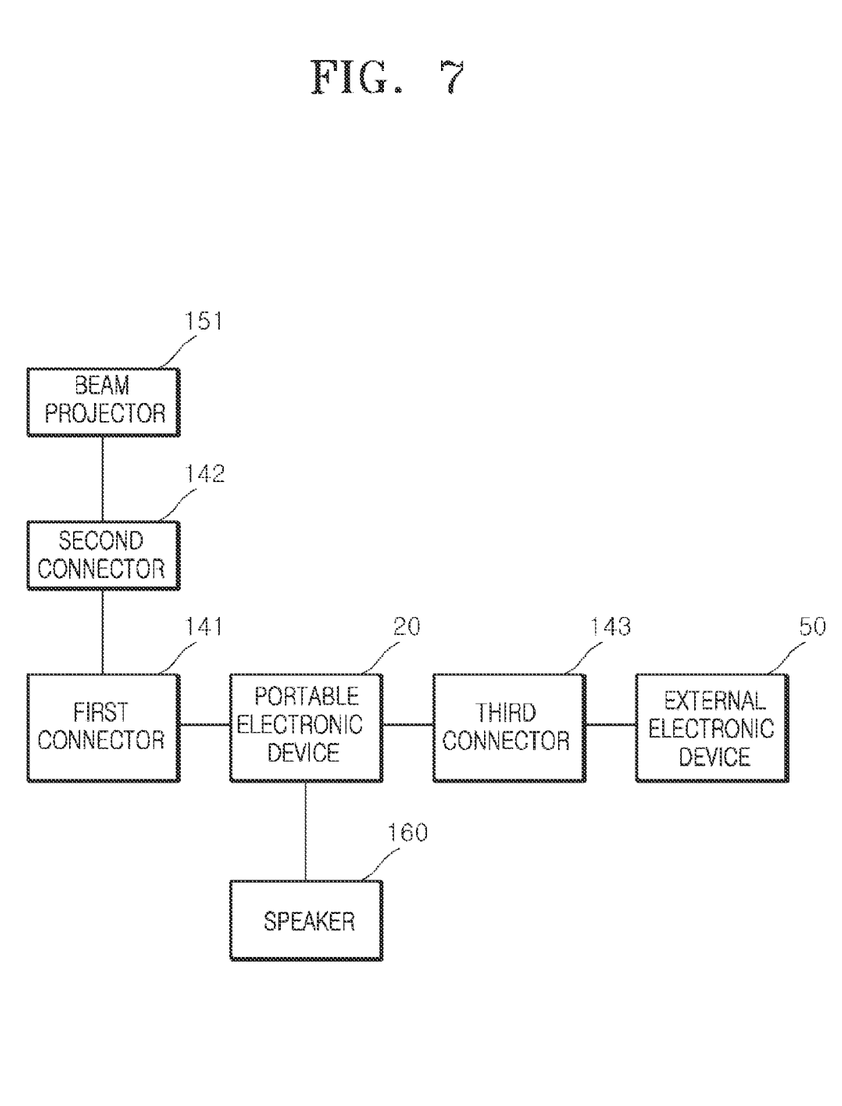
FIG. 7 is a block diagram illustrating an exemplary sterilization apparatus for a portable electronic device in accordance with the embodiment of the present disclosure.
Figure 8:
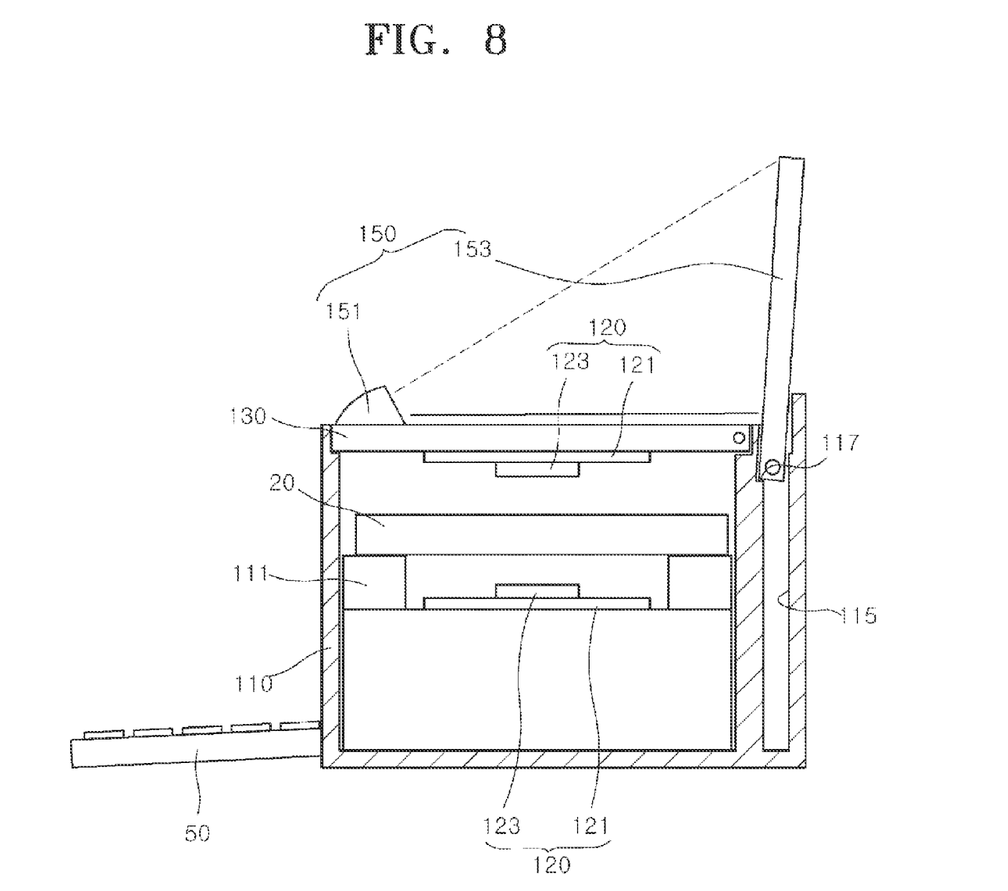
FIG. 8 is a schematic side view illustrating a state in which an external electronic device is connected to the sterilization apparatus for a portable electronic device in accordance with the embodiment of the present disclosure.

FIG. 5 is a schematic cross-sectional view illustrating the coupling structure of the screen in the sterilization apparatus for a portable electronic device in accordance with the embodiment of the present disclosure. FIG. 6 is a schematic side view illustrating a state in which the display unit is operated after the portable electronic device is put into the case of the sterilization apparatus for a portable electronic device in accordance with the embodiment of the present disclosure. FIG. 7 is a block diagram illustrating the sterilization apparatus for a portable electronic device in accordance with the embodiment of the present disclosure. FIG. 8 is a schematic side view illustrating the state in which an external electronic device is connected to the sterilization apparatus for a portable electronic device in accordance with the embodiment of the present disclosure.

Referring to FIGS. 5 to 8, the case 110 may have a housing groove 115 formed at one side of the case 110 so as to house the screen 153. The housing groove 115 may be formed in the entire part of one wall surface of the case 110. The screen 153 may be installed to be lifted and lowered in the housing groove 115. The screen 153 may be formed in a rectangular plate shape, and display an image. Since the screen 153 is installed to be lifted and lowered in the housing groove 115, the screen 153 may be inserted into the housing groove 115 of the case 110 when the screen 153 is not used, and moved toward the top of the case 110 when the screen 153 is used. The screen 153 may have a white color to clearly display an image.

The housing groove 115 may have a stepped part 117 formed at the top of the housing groove 115. The stepped part 117 has the width greater than that of the housing groove 115. When the screen 153 is lifted to the top, the bottom of the screen 153 may be supported on the stepped part 117. Thus, the screen 153 can be prevented from descending in the housing groove 115. When the bottom of the screen 153 is supported by the stepped part 117, the screen 153 may slightly lean toward one side.

Furthermore, the screen 153 may have protrusions 154 protruding to the outside and formed at both sides of the screen. The case 110 may have locking parts 114 formed at the top of the housing groove 115 such that the protrusions 154 of the screen 153 are locked to the respective locking parts 114. When the screen 153 is lifted, the protrusions 154 of the screen 153 may be locked to the locking parts 114 of the case 110, thereby preventing the screen 153 from being separated from the housing groove 115.

The operation of the sterilization apparatus for a portable electronic device in accordance with the embodiment of the present disclose will be described.

After the door 130 is opened, the portable electronic device 20 may be put into the case 110. At this time, the support parts may support the bottom surface of the portable electronic device 20. The connection part of the cable may connect the connector of the portable electronic device 20 to the first connector 141 of the case 110. Furthermore, the connection part of the cable may connect the connector of the portable electronic device to the third connector 143.

When the door 130 is closed, the first connector 141 of the case 110 and the second connector 142 of the door 130 may be connected to each other. Thus, the portable electronic device 20 may be connected to the beam projector 151 of the display unit 150 through the first and second connectors 141 and 142.

The UV irradiation unit 120 may be formed to correspond to the top and bottom of the portable electronic device 20. When a user manipulates the operation button arranged on the case 110, electricity may be supplied to the UV irradiation unit 120 such that the UV LEDs 123 emit UV light. As the UV light is irradiated onto the portable electronic device 20, the portable electronic device 20 may be sterilized.

Furthermore, when the first and second connectors 141 and 142 are connected as the door 130 is closed, the beam projector 151 may be driven, and the UV LEDs 123 may irradiate UV light.

While the portable electronic device 20 is sterilized in the case 110, a phone call may be received in the portable electronic device 20. At this time, the portable electronic device 20 may transmit an image to the beam projector 151 through the first and second connectors 141 and 142. The beam projector 151 may project the image onto the screen 153. Thus, even while the portable electronic device 20 is sterilized in the case 110, the user can be notified through the screen 153 that the portable electronic device 20 is ringing.

The user may connect the third connector 143 of the case 110 to the external connector of the external electronic device 50 using the connection part of the cable. Thus, the user may input data stored in the external electronic device 50 to the portable electronic device 20, or output data stored in the portable electronic device 20 to the external electronic device 50. Furthermore, the user may input data to the portable electronic device 20 through an input device such as a keyboard.

The third connector 143 may be connected to a charger through a charging connector such that the portable electronic device 20 can be charged. Furthermore, the portable electronic device 20 may be wirelessly charged.

The speaker 160 and the portable electronic device 20 may be connected to each other through the speaker connector. Thus, while the portable electronic device 20 is sterilized, the speaker 160 may be driven by the portable electronic device 20 such that the user can listen to music or voice.

As described above, since the portable electronic device 20 is sterilized by the UV LEDs 123, the portable electronic device 20 can be hygienically used.

Furthermore, since the screen related to the portable electronic device 20 is displayed on the display unit 150 while the portable electronic device 20 is sterilized, the user can recognize the operation state of the portable electronic device 20 even in a state where the portable electronic device 20 is put into the case 110.

Furthermore, even while the portable electronic device 20 is sterilized, the portable electronic device 20 and the external electronic device 50 may exchange data with each other.

While some embodiments of the disclosed technology have been disclosed for illustrative purposes above, those skilled in the art will appreciate that various modifications, additions and substitutions are possible, without departing from the scope and spirit of the disclosed technology as defined in the accompanying claims.

What is claimed is:

1. A sterilization apparatus for a portable electronic device, comprising:
   a case having an opening receiving a portable electronic device and including a housing groove formed on one side of the case;
   an ultraviolet (UV) irradiation unit arranged in the case, and configured to sterilize the portable electronic device by irradiating UV light onto the portable electronic device;
   a door connected to the case for opening and closing the opening of the case; and
   a display unit connected to the portable electronic device, and including a screen configured to display an image outputted from the portable electronic device, wherein the screen is shaped like a plate and is installed to be movable upward or downward via a linear movement along the housing groove along a plane that comprises the screen.

2. The sterilization apparatus of claim 1, further comprising:
   a first connector installed in the case and connected to a connector of the portable electronic device; and
   a second connector installed in the door and connected to the first connector and the display unit.

3. The sterilization apparatus of claim 2, wherein when the door is closed, the first and second connectors are connected to each other.

4. The sterilization apparatus of claim 2, further comprising a third connector installed in the case to connect the portable electronic device to an external electronic device.

5. The sterilization apparatus of claim 2, wherein the display unit comprises:
   a beam projector installed on the door, connected to the second connector, and configured to project an image outputted from the portable electronic device; and
   a screen installed in the case and displaying the image projected from the beam projector.

6. The sterilization apparatus of claim 1, wherein the UV irradiation unit is installed on the bottom of the case.

7. The sterilization apparatus of claim 1, further comprising additional UV irradiation unit arranged on the door to provide UV radiation to the portable electronic device.

8. The sterilization apparatus of claim 6, wherein the UV irradiation unit comprises:
   a printed circuit board; and
   UV LEDs mounted on the printed circuit board to irradiate UV light onto the portable electronic device.

9. The sterilization apparatus of claim 8, wherein a housing groove has a stepped part formed at the top of the housing groove with greater width than that of the housing groove, and
   the stepped part is configured to support the bottom of the screen such that the screen is prevented from descending from the housing groove.

10. A sterilization apparatus for a portable electronic device, comprising:
   a case having a bottom portion with sidewalls extending up from the bottom portion and configured to provide a space inside the case for mounting a portable electronic device, wherein the case provides a first connector connected with the portable electronic device;
   a UV LED arranged in the case and configured to provide UV radiation to the portable electronic device; and
   a cover arranged around a top portion of the case and providing a second connector connected with the first connector, wherein the connection between the first and second connectors allows the UV LED irradiating UV light,
   wherein the sterilization apparatus further includes a screen inserted into a groove formed at one sidewall of the case to be movable upward or downward in a linear translation motion along the groove along a plane that comprises the screen and displaying information of the portable electronic device during the sterilization.

11. The sterilization apparatus of claim 10, further comprising a third connector provided in the case and connected to an external electronic device.

12. The sterilization apparatus of claim 10, wherein the screen is movable along the sidewall of the case.

13. The sterilization apparatus of claim 10, information of the portable electronic device includes receiving a phone call or exchanging data with another device.

14. The sterilization apparatus of claim 10, further comprising a beam projector provided in the cover and connected to the portable electronic device and the screen, the beam projector projecting a screen of the portable electronic device onto the screen of the sterilization apparatus.

15. The sterilization apparatus of claim 10, wherein the case provides a stepped part formed at a top portion of the groove with a greater width than the groove.

16. The sterilization apparatus of claim 10, wherein the cover is configured to selectively cover the top portion.

17. The sterilization apparatus of claim 10, further comprising an additional UV LED arranged in the cover to provide UV radiation to the portable electronic device.

18. The sterilization apparatus of claim 10, further comprising a speaker provided in the case or the cover.

19. The sterilization apparatus of claim 10, wherein the screen has protrusions protruding to outside and formed at both sides of the screen.

20. A sterilization apparatus for a portable electronic device, comprising:

a case having an opening receiving a portable electronic device;
an ultraviolet (UV) irradiation unit arranged in the case, and configured to sterilize the portable electronic device by irradiating UV light onto the portable electronic device;
a door connected to the case for opening and closing the opening of the case;
a display unit connected to the portable electronic device, and configured to display an image outputted from the portable electronic device;
a first connector installed in the case and connected to a connector of the portable electronic device; and
a second connector installed in the door and connected to the first connector and the display unit;
wherein the display unit comprises:
a beam projector installed on the door, connected to the second connector, and configured to project an image outputted from the portable electronic device; and
a screen installed in the case and displaying the image projected from the beam projector,
wherein the case includes a housing groove formed at one side of the case and housing the screen, and the screen is installed to be movable upward or downward along the housing groove along a plane of the screen.

21. The sterilization apparatus of claim 20, wherein the screen moves along the side of the case.

22. The sterilization apparatus of claim 20, wherein the display unit operates to display the image only when the opening of the case is closed.

* * * * *